United States Patent
Sakagami et al.

[11] Patent Number: 6,004,906
[45] Date of Patent: Dec. 21, 1999

[54] PLANT GROWTH FACTOR

[75] Inventors: Youji Sakagami; Yoshikatsu Matsubayashi, both of Aichi, Japan

[73] Assignee: Kyowa Hakko Kogyo Co., Ltd., Japan

[21] Appl. No.: 08/949,038

[22] Filed: Oct. 10, 1997

Related U.S. Application Data

[63] Continuation-in-part of application No. PCT/JP95/02091, Oct. 12, 1995, and a continuation-in-part of application No. PCT/JP96/00994, Apr. 11, 1996.

[30] Foreign Application Priority Data

Apr. 12, 1995 [JP] Japan .................................... 7-086935

[51] Int. Cl.[6] .................................................. A01N 41/02
[52] U.S. Cl. ........................... 504/350; 504/349; 514/18; 530/330; 435/430
[58] Field of Search .............................. 530/330; 514/17, 514/18; 435/430; 504/350, 349

[56] References Cited

FOREIGN PATENT DOCUMENTS

| | | |
|---|---|---|
| 0 220 379 | 5/1987 | European Pat. Off. . |
| 0 448 093 A2 | 9/1991 | European Pat. Off. . |
| WO 94/11018 | 5/1994 | WIPO . |

OTHER PUBLICATIONS

Bellincampi, D. and Morpurgo, G., "Conditioning Factor Affecting Growth in Plant Cells in Culture," *Plant Science*, 51:83–91 (1987).

Lam, K.S., et al., "The Chemical Synthesis of Large Random Peptide Libraries and Their Use for the Discovery of Ligands for Macromolecular Acceptors," *Bioorganic & Medicinal Chem. L.*, 3:419–424 (1993).

Teasdale, R. and Richards, D., "Study of a factor produced by suspension–cultured *Pinus radiata* cells which enhances cell growth at low inoculum densities," *Plant Cell, Tissue and Organ Culture*, 26:53–59 (1991).

Dyson, H.J., et al., "Folding of Immunologic Peptide Fragments of Proteins in Water Solutions," *J. Mol. Biol.*, 201:161–200 (1988).

Birnberg, P.R., et al., "Characterization of Conditioning Factors that Increase Colony Formation from <<Black Mexican Sweet Corn>> Protoplasts," *J. Plant Physiol.*, 132:316–321 (1988).

Köhler, F. and Wenzel, G., "Regeneration of Isolated Barley Microspores in Conditioned Media and Trials to Characterize the Responsible Factor," *J. Plant Physiol.*, 121:181–191 (1985).

Echner, et. al. Chem. Abstr. No. 1984:121586, 1983.

Matsubayashi, et. al. Phytosulfokine, sulfated peptides that induce the proliferation of single mesophyll cells of *Asparagus officinalis* L. P.N.A.C. USA, (1996), 93(15), 7623, 1996.

Lou, et. al. Structure–activity relationship of a novel peptide substrate for p60c–src protein tyrosine kinase. Lett. Pept. Sci. (1996), 2(5), 289; Chem. Abstr. No. 1996:86343, 1996.

Groeger, et. al. Chem. Abstr. No. 1990:424507, 1989.

Dyson, et. al. Folding of immunogenic peptide fragments of proteins in water solution I. Sequence requirements for the formation of a reverse turn. J. Mol Biol. (1988), 201(1), 161–200, 1988.

Karelin, et. al. Chem. Abstr. No. 1992:543989, 1992.

Novak, et. al. Chem. Abstr. No. 1975:150793, 1975.

K. Barlos et al., "Application of 2–chlorotrityl resin in solid phase synthesis of (Leu[15])–gastrin 1 and unsulfated cholecystokinin octapeptide", *International Journal of Peptide and Protein Research* 38:555–561 (December 1991).

R.L. Novak et al., "Tyrosyl Peptide Models for Acidic Protein–DNA Interactions", *Nature New Biology* 243:155–157 (1973).

Supplemental European Search Report in EP 96 909341.

*Primary Examiner*—Cecilia J. Tsang
*Assistant Examiner*—Fabian Jameison
*Attorney, Agent, or Firm*—Finnegan, Henderson, Farabow, Garrett & Dunner, L.L.P.

[57] ABSTRACT

The present invention relates to a peptide of the formula:

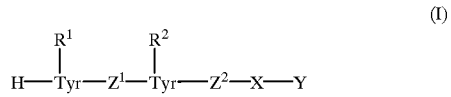

(I)

wherein $R^1$ and $R^2$ are the same or different and each represents $SO_3H$ or H; X represents an α-amino acid or a single bond; $Z^1$ and $Z^2$ are the same or different and each represents an α-amino acid; and Y represents OH or $NH_2$. This peptide has plant growth factor properties.

14 Claims, 2 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS:
      (D) TOPOLOGY: linear    (ii) MOLECULE TYPE: peptide    (ix) FEATURE:
      (A) NAME/KEY: Modified-site
      (B) LOCATION: 1
      (D) OTHER INFORMATION: /note= "Xaa means O-sulfotyrosine."

(ix) FEATURE:
      (A) NAME/KEY: Modified-site
      (B) LOCATION: 3
      (D) OTHER INFORMATION: /note= "Xaa means O-sulfotyrosine."

(xi) SEQUENCE DESCRIPTION: SEQ ID NO:1:

Xaa Ile Xaa Thr Gln
1               5

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa mean O-sulfotyrosine."

(ix) FEATURE:
        (A) NAME/KEY: Modified-site
        (B) LOCATION: 3
        (D) OTHER INFORMATION: /note= "Xaa means O-sulfotyrosine."

(xi) SEQUENCE DESCRIPTION: SEQ ID NO:2:

Xaa Ile Xaa Thr
1

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa means O-sulfotyrosine."

(ix) FEATURE:
        (A) NAME/KEY: Modified-site
        (B) LOCATION: 3
        (D) OTHER INFORMATION: /note= "Xaa means O-sulfotyrosine."

(xi) SEQUENCE DESCRIPTION: SEQ ID NO:3:

Xaa Ile Xaa Thr Gln
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa means O-sulfotyrosine."

(ix) FEATURE:
        (A) NAME/KEY: Modified-site
        (B) LOCATION: 3
        (D) OTHER INFORMATION: /note= "Xaa means O-sulfotyrosine."

(xi) SEQUENCE DESCRIPTION: SEQ ID NO:4:

```
Xaa Val Xaa Thr Gln
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa means O-sulfotyrosine."

(ix) FEATURE:
        (A) NAME/KEY: Modified-site
        (B) LOCATION: 3
        (D) OTHER INFORMATION: /note= "Xaa means O-sulfotyrosine."

(xi) SEQUENCE DESCRIPTION: SEQ ID NO:5:

Xaa Ile Xaa Ser Gln
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa means O-sulfotyrosine."

(xi) SEQUENCE DESCRIPTION: SEQ ID NO:6:

Xaa Ile Tyr Thr Gln
1               5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Xaa means O-sulfotyrosine."

(xi) SEQUENCE DESCRIPTION: SEQ ID NO:7:

Tyr Ile Xaa Thr Gln
1               5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: linear
```

```
        (ii) MOLECULE TYPE: peptide (xi) SEQUENCE DESCRIPTION: SEQ ID NO:8:

Tyr Ile Tyr Thr Gln
1               5

(2) INFORMATION FOR SEQ ID NO:9:

(i) SEQUENCE CHARACTERISTICS:
                (A) LENGTH: 5 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note= "Xaa means O-sulfotyrosine or
                    tyrosine."

(ix) FEATURE:
                (A) NAME/KEY: Modified-site
                (B) LOCATION: 2
                (D) OTHER INFORMATION: /note= "Xaa means an aliphatic amino
                    acid."

(ix) FEATURE:
                (A) NAME/KEY: Modified-site
                (B) LOCATION: 3
                (D) OTHER INFORMATION: /note= "Xaa means O-sulfotyrosine or
                    tyrosine."

(ix) FEATURE:
                (A) NAME/KEY: Modified-site
                (B) LOCATION: 4
                (D) OTHER INFORMATION: /note= "Xaa means an aliphatic amino
                    acid."

(ix) FEATURE:
                (A) NAME/KEY: Modified-site
                (B) LOCATION: 5
                (D) OTHER INFORMATION: /note= "Xaa means an aliphatic amino
                    acid or single bond."

(xi) SEQUENCE DESCRIPTION: SEQ ID NO:9:

Xaa Xaa Xaa Xaa Xaa
1               5
```

PLANT GROWTH FACTOR

CROSS-REFERENCES

This is a continuation-in-part of International Applications Nos. PCT/JP95/02091 filed on Oct. 12, 1995, PCT/JP96/00994 filed on Apr. 11, 1996, and JP 86935 filed on Apr. 12, 1995.

FIELD OF THE INVENTION

The present invention relates to peptides having the properties of a plant growth factor.

BACKGROUND OF THE INVENTION

The following plant-derived plant growth factors are known: barley-derived, fat-soluble fatty acid having a molecular weight of 600 or less (Journal of Plant Physiology, Vol. 121, pp. 181–191, 1985); pine-derived growth factor consisting of oligosaccharides having a molecular weight of 1000 or less (Plant Cell, Tissue and Organ Culture, Vol. 26, pp. 53–59, 1991); carrot-derived, heat-stable growth factor having a molecular weight of about 700 (Plant Science, Vol. 51, pp. 83–91, 1987); and black Mexican maize-derived growth factor which has a molecular weight of 1350 or less, oligosaccharide-like characteristics, and is not adsorbed to either of anion-exchange resin or cation-exchange resin in a buffer at pH of 5 (Journal of Plant Physiology, Vol. 132, pp. 316–321, 1988).

It is difficult to isolate and purify such known plant-derived plant growth factors, and there is no known technique for mass-production of these factors. In order to effectively use a plant growth factor as a plant cell growth promoter, it must be mass-producible.

SUMMARY OF THE INVENTION

The present invention relates to peptides having the properties of a plant growth factor and of the formula (I)

wherein $R^1$ and $R^2$ are the same or different and each represents $SO_3H$ or H; X represents an α-amino acid or a single bond; $Z^1$ and $Z^2$ are the same or different and each represents an α-amino acid; and Y represents OH or $NH_2$. This peptide has plant growth factor properties.

BRIEF DESCRIPTION OF THE DRAWINGS

Each symbol in FIG. 1 means as follows:
- --□--: CM 25.0%
- —◇—: CM 12.5%;
- —○—: CM 6.3%;
- —△—: CM 3.1%;
- —■—: CM 1.6%; and
- —◆—: control.

Each symbol in FIG. 2 means as follows:
- --□--: compound (I-1);
- —◇—: compound (I-2);
- —○—: compound (I-3);
- —△—: compound (I-6);
- —■—: compound (I-7); and
- —◆—: compound (I-8).

FIG. 3-*a* shows the elution pattern of plant growth factors in DEAE Sephadex A-25 ion-exchange chromatography; FIG. 3-*b* shows the elution pattern of plant growth factors in Bio-Gel P-2 extra fine chromatography; and FIG. 3-*c* shows the elution pattern of plant growth factors in Develosil ODS-HG-5 reversed-phase HPLC.

In the figures, the bars indicate the colony formation frequency; and the lines indicate the absorbance (at 220 nm).

DETAILED DESCRIPTION OF THE INVENTION

The present invention relates to peptides of formula (I):

(I)

SEQ ID NO: 9 wherein $R^1$ and $R^2$ are the same or different and each represents $SO_3H$ or H; X represents an α-amino acid or a single bond; $Z^1$ and $Z^2$ are the same or different and each represents an α-amino acid; and Y represents OH or $NH_2$.

Compounds of formula (I) are hereinafter referred to as compound (I). In the definition of $R^1$ and $R^2$, it is preferred that at least one of $R^1$ and $R^2$ is $SO_3^{-2}$. In the definitions of the groups in formula (I), α-amino acid means aliphatic amino acid such as glycine, alanine, valine, leucine and isoleucine; hydroxyamino acid such as serine and threonine; sulfur-containing amino acid such as cysteine, cystine and methionine; acidic amino acid such as aspartic acid and glutamic acid; amido-amino acid such as asparagine and glutamine; basic amino acid such as lysine, arginine and ornithine; aromatic amino acid such as phenylalanine and tyrosine; and heterocyclic amino acid such as histidine, tryptophan, proline and hydroxyproline. Among these α-amino acids for X, preferred are amido-amino acids, especially preferred is glutamine. Among these α-amino acids for $Z^1$, preferred are aliphatic amino acids, especially preferred are valine and isoleucine. Among these α-amino acids for $Z^2$, preferred are hydroxyamino acids.

Compound (I) is a plant growth factor that can be obtained through extraction from higher plants or through ordinary peptide synthesis.

Plants from which the plant growth factors of the present invention can be extracted may be any monocotyledon including asparagus, rice and maize, preferably liliaceous plants such as asparagus. The extraction can be conducted by an extraction method using aqueous media (Plant Cell Tissue Culture, written by Harada & Komamine, 1979, published by Rikohgaku-sha, p. 382), or a method for collecting active fractions from cultures of cultivated cells (Plant Cell Tissue Culture, written by Harada & Komamine, 1979, published by Rikohgaku-sha, p. 27).

The present plant growth factors may promote the cell growth in all plant cells, and are particularly effective in the promotion of the cell growth of monocotyledons such as asparagus, rice and maize.

As a method for extraction of a plant growth factor from higher plants, the following method may be applied: cells to be cultivated are collected from a higher plant by an ordinary method (Plant Cell Tissue Culture, written by Harada & Komamine, 1979, published by Rikohgaku-sha, p. 27), the collected cells are implanted in a medium that is used for ordinary plant cell cultivation (Plant Science, Vol. 65, pp. 111–171, 1989), and cultured therein with shaking at 20 to 30° C., preferably at 24 to 28° C., for 8 to 16 days, preferably for 9 to 11 days. After the shaking cultivation, the culture medium is separated from the cells through centrifugation, etc., to obtain a conditioned medium (hereinafter referred to as CM).

An anion-exchange resin such as DEAE Sephadex A-25, DEAE cellulose and DEAE Sepharose is swollen with a buffer (pH of 6.5 to 8.0) such as 10 to 100 mM tris-HCl buffer, phosphate buffer and sodium carbonate-carbonic acid buffer. Then, the plant growth factors contained in CM are adsorbed to the anion-exchange resin by a column method or a batch method. Next, the plant growth factors may be collected through elution with salts such as potassium chloride and sodium carbonate, with stepwise increasing the salt concentration from 10 to 2000 mM. The plant growth factors are eluted at a salt concentration of 800 to 2000 mM, preferably 1000 to 1250 mM.

The resulting fractions are then desalted through dialysis or the like, and thereafter applied to a gel permeation column, preferably Bio-Gel P2, Bio-Gel P4 (both produced by Bio Rad), Sephadex G25 (produced by Pharmacia) or the like.

The active fractions thus desalted through such dialysis and gel permeation are then fractionated using reversed-phase high performance liquid chromatography (reversed-phase HPLC) with Nucleosyl-100-C18 (produced by Nagel), Microsolve PR18 (produced by Merck) or the like as the carrier. The purified plant growth factors are obtained from the fractions at a retention time between 8 and 12 minutes, which are eluted with a solvent of water-acetonitrile, water-methanol, water-ethanol or the like containing trifluoroacetic acid (TFA).

Apart from the above, compound (I) can be produced according to peptide synthesis, which is referred to, for example, "Peptide Synthesis", in N. Izumiya et al. (published by Maruzen Publishing, in 1975) as follows: A peptide skeleton is synthesized, and the skeleton is sulfated with an enzyme capable of bonding sulfate group to the side chain of tyrosine residue such as arylsulfotransferase to obtain the intended peptide.

Compound (I) can be used as a plant growth promoter as shown in the following embodiments.

(1) Liquid Preparations:

Compound (I) is dissolved in an aqueous solution containing a preservative and a pH adjusting agent at a concentration of 0.0001 to 1% to prepare a plant cell growth promoter. The preservative includes one or more of boric acid, bleaching powder, benzoic acid, salicylic acid, sorbic acid, dehydroacetic acid, propionic acid, isocyanuric acid, chlorous acid, hypochlorous acid, p-hydroxybenzoic acid and its esters, tribromosalicylanilide, 3,4,4'-trichlorocarbanilide, hexachlorophene, bithionol, chloramine-T, chloramine-B and halazone. Among these, preferred is sorbic acid. As a pH adjusting agent, any conventionally used pH adjusting agent such as citrates and phosphates can be used either singly or in combination.

The liquid preparation thus obtained is diluted from 100-fold to 10000-fold, preferably 1000-fold. Plant seeds or seedlings such as cuttings are dipped in the resulting dilution, or the dilution is added to water cultures at a final concentration of the peptide of 0.001 to 10 ppm. In that manner, compound (I) can be used as a plant growth promoter.

(2) Paste Preparations:

A peptide of compound (I) is kneaded with a paste base at a concentration of 0.01 to 10 ppm to prepare a plant growth promoter. The paste base includes one or more of fats, fatty oils, lanolin, vaseline, paraffin, wax, resins, plastics, glycol, higher alcohols and glycerin. Among them, preferred are petroleum jelly such as VASELINE™ and lanolin.

The paste preparation thus obtained is applied to the grafted portions of grafts, or to the peduncles of fruits, or to the cut surfaces of cuttings. In that manner, compound (I) can be used as a plant growth promoter.

Embodiments of compound (I) are shown below.

(COMPOUND I-1)
(SEQ ID NO: 1)

(COMPOUND I-2)
(SEQ ID NO: 2)

(COMPOUND I-3)
(SEQ ID NO: 3)

(COMPOUND I-4)
(SEQ ID NO: 4)

(COMPOUND I-5)
(SEQ ID NO: 5)

(COMPOUND I-6)
(SEQ ID NO: 6)

(COMPOUND I-7)
(SEQ ID NO: 7)

(COMPOUND I-8)
(SEQ ID NO: 8)

EXAMPLES

The plant cell growth activity of the present plant growth factors is shown in the following examples.

Example 1

Plant Cell Growth Activity

Single asparagus cells, as obtained according to the method of Example 4, were implanted in the media, as prepared by the method of Example 5, and incubated with the present plant growth factor in the media. The influence of the plant growth factor on the proliferation of the incubated asparagus cells was determined by measuring the change in the colony formation frequency in each medium.

(i) Incubation of Cells:

Cells were incubated in a 24-well microtiter plate (IWAKI 3820-024). To each well of the microtiter were added 250 μl of a suspension of single asparagus cells as prepared at a cell density of 2-fold the intended final cell density, 125 μl of the liquid medium having a concentration of 4-fold the intended final concentration, and 125 μl of sterilized distilled water or 125 μl of CM as obtained in Example 6, sterilized through filtration (ADVANTEC DISMIC-13cp, 0.20 μm) and diluted just before use, and fully stirred. Then, the plates were sealed with vinyl tape in order to prevent vaporization, in which the cells were incubated in the dark at 28° C. with shaking at 120 rpm (TAITEC BR-300L).

(ii) Observation of Cells:

Using an inverted microscope (100-magnification, OLYMPUS CK2), the number of the living cells (including the colony-forming cells), the number of the dead cells, and the number of the colony-forming cells, which were observed in the field of view, were counted for each well. On the basis of the data thus obtained for 3 wells or more, the colony formation frequency (C) and the cell viability (L) were calculated according to the following equations.

$$C(\%) = a/b \times 100$$

C: colony formation frequency
a: number of colony-forming cells
b: number of living cells $$L(\%) = [b/(b+d)] \times 100$$

L: cell viability
b: number of living cells
d: number of dead cells (iii) Effect of CM on Colony Formation:

CM was added to the cultures of single asparagus cells of $5.0 \times 10^4$ cells/ml and $2.5 \times 10^4$ cells/ml, at a final CM concentration of 25.0%, 12.5%, 6.3%, 3.1%, or 1.6%, and the cells were incubated. The colony formation frequency for the asparagus cells at each CM concentration was determined. The results are shown in FIG. 1.

Hereinafter, the above-mentioned process is referred to as the bioassay of the plant growth factors.

Figure 1:
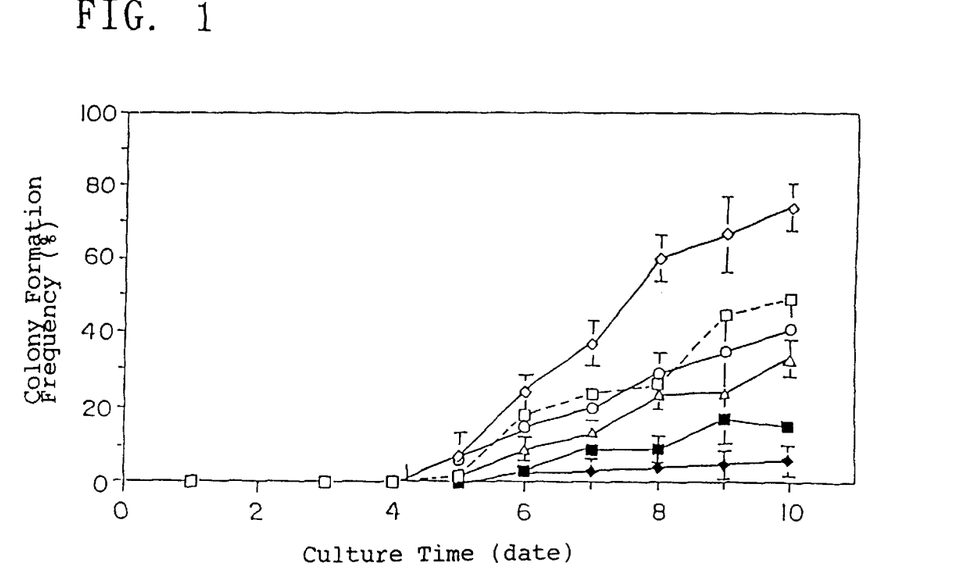
FIG. 1 shows the influence of conditioned medium (hereinafter "CM") concentration on the colony formation frequency for asparagus-derived, incubated cells.

FIG. 1 indicates that the colony formation frequency increased significantly depending on the CM concentration. It is therefore evident that CM has the activity of promoting the growth of plant cells.

Example 2
Plant Cell Growth Activity

Figure 2:
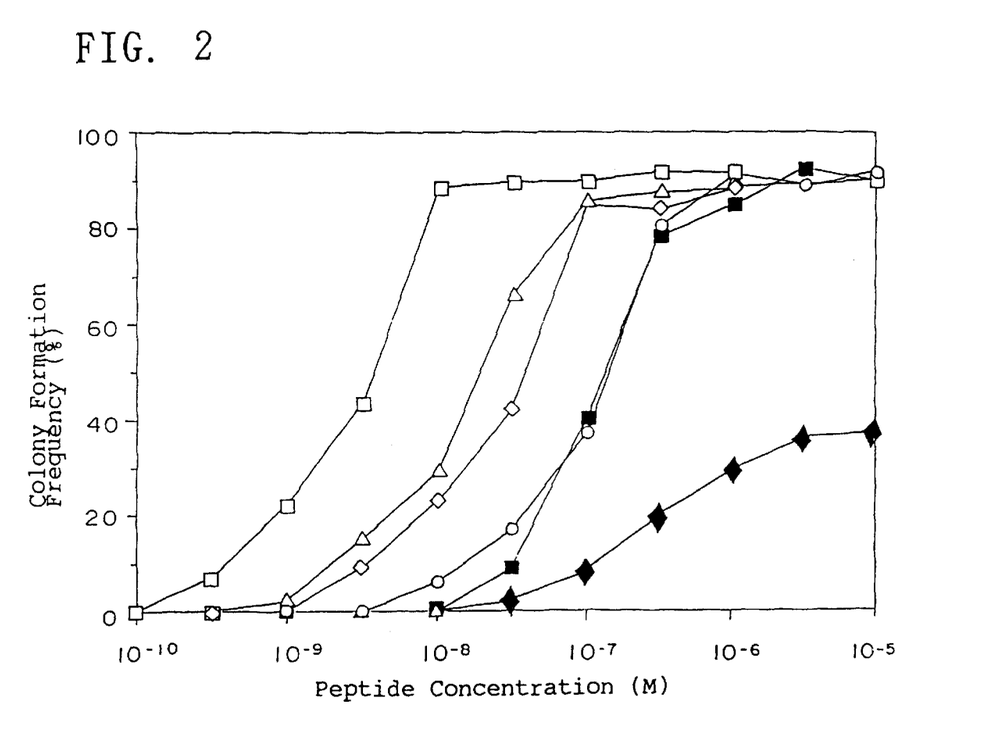
FIG. 2 shows the influence of the concentrations of compound (I-1), compound (I-2), compound (I-3), compound (I-6), compound (I-7) and compound (I-8) on the colony formation frequency for asparagus-derived, incubated cells.

The cell growth-promoting activity was measured by the same process as in Example 1, except that compound (I-1), compound (I-2), compound (I-3), compound (I-6), compound (I-7) or compound (I-8) (from $10^{-9}$ M to $10^{-5}$ M) were used herein. The results are shown in FIG. 2.

Examples Regarding Extraction of CM, and Physico-chemical Properties Thereof

Example 3
Plant Material

Seeds of asparagus (*Asparagus officinalis* L. cv. Mary Washington 500W; Takii Seeds and Seedlings) were seeded in nursery pots (diameter: 9 cm) filled with Kureha culture soil (Kureha Chemical Industry), and grown in an air-conditioned room (Koito Industry). In the air-conditioned room, the illumination intensity was 20,999 Lux on the surfaces of the leaves, the lighting time was 16 hours/day as the light period, and 8 hours/day as the dark period. The temperature was 22° C. in the daytime and 18° C. in the nighttime, and the humidity was about 80%. The seeds normally germinate in about 3 weeks after the seeding, and put forth about 3 buds within 6 weeks after the seeding. Then, the seedlings grown in the pots were transplanted into planters having a diameter of 21 cm, as required. The cladodes collected from the seedlings grown for 9 weeks after the seeding were used in the following experiments.

Example 4
Preparation of Mesophyll Cells

One cladode of asparagus having a length of about 10 cm was used for bioassay, and for preparing CM, used were four such cladodes per 200 ml of CM. The collected cladodes were dipped in 70% ethanol for 30 seconds, then sterilized in a solution of 10-fold diluted antiformin containing Tween 20 (2 drops/100 ml) for 10 minutes, and thereafter washed three times with sterilized distilled water. Next, the cladodes were homogenized with sterilized distilled water using a glass homogenizer (22×167 mm; Iwaki Glass) on a clean bench. Then, the resulting homogenate was filtered through a 37 μm stainless mesh (Iida Manufacturing), and the filtrate was centrifuged (100×g, 3 min; Kubota KS-5000) to precipitate the single cells. The precipitated single cells were again suspended in sterilized distilled water, and then centrifuged to remove the supernatant. This process was repeated three times, whereby impurities were completely removed from the cells.

Example 5
Preparation of Medium

The composition of the medium to be used herein is shown in Table 1.

TABLE 1

Composition of Culture Medium

| Macro Elements | (mg/liter) | Micro Elements | (mg/liter) | Organic Components | |
|---|---|---|---|---|---|
| | | $FeSO_4 7H_2O$ | 27.8 | Myo-inositol | 100 mg/liter |
| | | $EDTA2Na2H_2O$ | 37.3 | Thiamine | 0.1 mg/liter |
| $KNO_3$ | 950 | $MnSO_4 H_2O$ | 16.9 | Glutamine | 1.0 g/liter |
| $NH_4NO_3$ | 825 | $ZnSO_4 7H_2O$ | 8.6 | | |
| $KH_2PO_4$ | 85 | $H_3BO_3$ | 6.2 | NAA | 1.0 mg/liter |
| $CaCl_2 2H_2O$ | 220 | $CuSO_4 5H_2O$ | 0.025 | BA | 0.3 mg/liter |
| $MgSO_4 7H_2O$ | 185 | $Na_2MoO_4 2H_2O$ | 0.25 | | |
| | | KI | 0.83 | Sucrose | 10 g/liter |
| | | $CoCl_2 6H_2O$ | 0.025 | Mannitol | 30 g/liter |

Just before use, the liquid medium having the composition shown in Table 1 was diluted with distilled water to have a concentration of 4-fold the intended concentration, adjusted to pH 5.8 with 1.0 N KOH, and then sterilized by filtering it through a sterilizing filter (ADVANTEC DISMIC-25cs, 0.20 μm).

Example 6
Collection of CM

The single cell suspension prepared above was conditioned to have a cell concentration of about $5.0 \times 10^5$ cells/ml, using a Bürker-Türk counting chamber (Nippon Rinsho Kikai Kogyo). To a 300-ml Erlenmeyer were put 50 ml of the suspension and 50 ml of the liquid medium having a 2-fold concentration (total: 100 ml), and sealed up with a silicone stopper. The cells were incubated in the dark at 28° C. with shaking at 120 rpm (TB-25R; Takasaki Kagaku Kikai). On the 10th day from the start of the incubation, the growth of the cells became the highest, CM was collected from the culture through suction filtration (ADVANTEC No. 2), then frozen and stored at −30° C.

The physico-chemical properties of the obtained CM are described in detail.

(a) Thermal Stability:

1.5 ml of CM was collected on the 10th day from the start of the incubation (the same CM is used hereinafter) was diluted 2-fold with 1.5 ml of distilled water, then heated in a boiling bath for 10 minutes and thereafter immediately cooled. In the same manner, 1.5 ml of CM was diluted 2-fold with distilled water, and autoclaved at 121° C. for 20 minutes.

These two samples were bioassayed.

CM as heated in the boiling bath for 10 minutes retained 70% of the cell growth-promoting activity, while CM as autoclaved at 121° C. for 20 minutes was completely deactivated.

(b) pH Stability:

1.0 ml of CM was diluted with distilled water to 4.0 ml, and adjusted to pH 3.0, pH 5.0, pH 7.0, pH 9.0 and pH 11.0 with 0.1 N $HNO_3$ or 0.1 N KOH. Then, these samples were kept at 4° C. for 24 hours. Then, each of these samples was adjusted to pH 5.8 with 0.1 N KOH or 0.1 N $HNO_3$, and then concentrated to 2.0 ml. These samples were then bioassayed. The initial pH of the CM itself was about 5.0.

The present plant growth factors were almost stable at pH 3.0, pH 5.0, pH 7.0 and pH 9.0. At pH 11.0, their activity was reduced to about 60%.

(c) Solvent Fractionation of CM:

2.0 ml of CM was diluted to 10 ml with distilled water, then adjusted to pH 3.0 with 0.1 N $HNO_3$, and extracted three times with 5.0 ml of ethyl acetate. The resulting aqueous layer was adjusted to pH 5.8 with 0.1 N KOH, and then concentrated to 4.0 ml. The ethyl acetate layer was dried with sodium sulfate, then evaporated to dryness, and dissolved in 4.0 ml of distilled water. In the same manner, 2.0 ml of CM was diluted to 10 ml with distilled water, then adjusted to pH 11.0 with 0.1 N KOH, and extracted three times with 5.0 ml of diethyl ether. The resulting aqueous layer was adjusted to pH 5.8 with 0.1 N $HNO_3$, and then concentrated to 4.0 ml. The ether layer was dried with sodium sulfate, then evaporated to dryness, and dissolved in 4.0 ml of distilled water. These four samples were bioassayed.

Under both the acidic condition and the basic condition, the aqueous layers retained the cell growth-promoting activity.

(d) Adsorption and Desorption Test for Reverse Phase Carriers:

Cosmosil $75C_{18}$-OPN (10 g)(Nacalai Tesque) was suspended in methanol, degassed in a vacuum, and filled into a column (1.7×8 cm; 18 ml). After the carrier was filled completely, the eluent in the column was replaced with distilled water, and the column was washed with 100 ml of distilled water. Then, 5.0 ml of CM was put into the column, and eluted with 100 ml of distilled water, 100 ml of 30% $CH_3CN$, and 100 ml of 60% $CH_3CN$ in order (flow rate: 60 ml/hour). The resulting fractions were evaporated to dryness using an evaporator, dissolved in 10 ml of distilled water, and bioassayed. In the same manner, 10 g of Diaion HP-20 (Mitsubishi Chemical) was suspended in methanol, degassed in a vacuum, and filled into a column. In order to prevent the carrier from floating up, sea sand B was layered over the carrier in the column at a thickness of 5 mm. The eluent in the column was replaced with distilled water, and the column was washed with 100 ml of distilled water. Then, 5.0 ml of CM was put into the column, and eluted with 100 ml of distilled water, 100 ml of 30% $CH_3CN$, and 100 ml of 60% $CH_3CN$ in order (flow rate: 60 ml/hour). The resulting fractions were evaporated to dryness using an evaporator, dissolved in 10 ml of distilled water, and bioassayed.

The plant growth factors were not retained by any of Cosmosil $75C_{18}$-OPN and Diaion HP-20, but were eluted out of the columns with distilled water. It is therefore evident that the present plant growth factors have relatively high polarity.

(e) Adsorption and Desorption Test for Activated Charcoal:

Activated charcoal (5.0 g)(Wako Pure Chemical Industry) was heated in 100 ml of 15% acetic acid at 100° C. for 30 minutes to thereby remove impurities therefrom, washed with 500 ml of distilled water, and suspended in distilled water. The resulting suspension was filled into a column (1.7×11 cm; 25 ml). Then, 5.0 ml of CM was put into the column, and then eluted with 100 ml of distilled water, 100 ml of 15% ethanol, 100 ml of 30% ethanol, and 100 ml of acetone in order (flow rate: 60 ml/hour). The resulting fractions were evaporated to dryness using an evaporator, dissolved in 10 ml of distilled water, and bioassayed.

The present plant growth factors were very strongly adsorbed to the activated charcoal, and were not eluted out at all with any of 15% ethanol, 30% ethanol and acetone, while it is generally known that, in this condition, neutral oligosaccharides and some acidic saccharides are eluted out.

(f) Adsorption and Desorption Test for Ion-exchange Resins:

DEAE Sephadex A-25 (0.8 g)(Pharmacia LKB Biotechnology) was swollen in 50 ml of 500 mM Tris-HCl buffer (pH 7.4) at room temperature for 24 hours, then suspended in the same buffer of 20 mM, and filled into a column (1.2×3.5 cm; 4.0 ml). Then, 10 ml of CM was lyophilized, and the resulting lyophilisate was dissolved in 10 ml of the same buffer. Then, the solution was put into the column, and eluted with 20 ml of the same buffer, 20 ml of the same buffer containing 250 mM KCl, 20 ml of the same buffer containing 500 mM KCl, and 20 ml of the same buffer containing 1000 mM KCl in order (flow rate: 15 ml/hour). Then, each eluate fraction was concentrated to 10 ml, and injected into a dialysis tube (Spectra/Por 7 MWCO: 1000), the both ends of which were closed with closers. These tubes were put in 3000 ml of distilled water at 4° C. for 24 hours for dialysis to desalt the fractions. Each dialysate was concentrated to 10 ml, and then bioassayed.

In the same manner, 0.8 g of CM Sephadex C-25 was swollen in 50 ml of 500 mM $KH_2PO_4$-KOH buffer (pH 6.0) at room temperature for 24 hours, then suspended in the same buffer of 20 mM, and filled into a column (1.2×3.5 cm; 4.0 ml). Then, 10 ml of CM was lyophilized, and the resulting lyophilisate was dissolved in 10 ml of the same buffer. The solution was put into the column, and eluted with 20 ml of the same buffer, and 20 ml of the same buffer containing 250 mM KCl in order (flow rate: 15 ml/hour). Each eluate fraction was desalted through dialysis, and then bioassayed.

The present plant growth factors were very strongly adsorbed to Sephadex A-25 and eluted with 1000 mM KCl. On the other hand, they were not adsorbed at all to CM Sephadex C-25. The present plant growth factors were eluted with 20 mM $KH_2PO_4$-KOH buffer. These results suggest that the present plant growth factors are acidic substances.

(g) Deactivation Test of Active Substances with Various Hydrolases:

A non-specific peptidase, Pronase E (3.0 mg)(Sigma), was dissolved in 3.0 ml of 20 mM $KH_2PO_4$-KOH buffer (pH 7.5). The precipitate was removed by filtration through a cellulose acetate filter (ADVANTEC DISMIC-13cp, 0.20 µm) to prepare an enzyme solution. A portion (1.0 ml) of the enzyme solution was heated in a boiling bath for 10 minutes to prepare a deactivated enzyme solution. Into the test tubes were put 0.9 ml of the same buffer, 1.0 ml of CM or distilled water, and 100 µl of the enzyme solution or the deactivated enzyme solution or the same buffer, and shaken in a thermostat shaker (TAITEC, Personal-11) at 37° C. at 170 rpm for 3 hours. After the enzymatic reaction, the reaction liquids were adjusted to pH 5.8 with 0.1 N $HNO_3$, then heated in a boiling bath for 10 minutes, and thereafter immediately cooled with ice, thereby deactivating the enzyme. After the deactivation, these samples were bioassayed.

In the same manner, 3.0 mg of Glycosidases "Mixed" (Seikakagu Kogyo), which is a mixture of several glycosidases, was dissolved in 3.0 ml of 20 mM glutamic acid-KOH buffer (pH 4.0), and filtered through a cellulose nitrate filter to remove impurities therefrom to prepare an enzyme solution. A portion (1.0 ml) of the enzyme solution was heated in a boiling bath for 10 minutes to prepare a deactivated enzyme solution. To the test tubes were added 0.9 ml of the same buffer, 1.0 ml of CM or distilled water, and 100 µl of the enzyme solution or the deactivated enzyme solution or the same buffer, and shaken in a thermostat shaker at 37° C. at 170 rpm for 3 hours. After the enzymatic reaction, the reaction liquids were adjusted to pH 5.8 with 0.1 N KOH, then heated in a boiling bath for 10 minutes, and thereafter immediately cooled with ice, thereby deactivating the enzyme. After the deactivation, these samples were bioassayed.

The present plant growth factors were completely deactivated when treated with the peptidase Pronase E. Accordingly, it is evident that these factors have a peptide structure in their molecule, and this peptide structure moiety is important for the factors to express their activity.

On the other hand, the present plant growth factors still kept their activity, even after having been treated with the mixture of glycosidases, Glycosidases "Mixed".

The above-mentioned physico-chemical properties of CM are summarized as follows.

1. Solubility:
   CM is easily soluble in water, but is hardly soluble in ethanol and acetone.
2. Differentiation in Acidic, Neutral or Basic Property:
   CM is acidic.
3. Thermal Stability:
   CM keeps 70% of its activity, after being heated at 100° C. for 10 minutes.

It is deactivated, after being autoclaved at 121° C. for 20 minutes.
4. Polarity:
   CM is a polar substance, and is not retained in reversed-phase columns with Cosmosil $75C_{18}$-OPN and Diaion HP-20.
5. pH Stability:
   CM is stable at pH of 3 to 9. At pH 11, its activity is reduced to 60%.
6. Action of Enzymes:
   CM is deactivated by Pronase E, but its activity is still kept even when treated with Glycosidases "Mixed".
7. Action to Ion-exchange Resins:
   CM is strongly adsorbed to DEAE Sephadex A-25 (and eluted with 1000 mM KCl), but it is not adsorbed at all to CM Sephadex C-25.

Examples Regarding Extraction, Synthesis and Sequencing of Compound (I)

Example 7

Isolation of Active Fractions from CM

DEAE Sephadex A-25 (3.0 g) was swollen in 50 ml of 500 mM Tris-HCl buffer (pH 7.4) at room temperature for 24 hours, suspended in the same buffer of 20 mM, and filled into a column (1.7×8.0 cm; 18 ml). Then, 100 ml of CM was concentrated to 50 ml using an evaporator, and Tris was added thereto at a final concentration of 20 mM. The solution was adjusted to pH 7.4 with 6 N HCl. Then, CM was put into the column, and six fractions were eluted as follows: with 30 ml of the same buffer, 30 ml of the same buffer containing 250 mM KCl, 30 ml of the same buffer containing 500 mM KCl, 30 ml of the same buffer containing 750 mM KCl, 30 ml of the same buffer containing 1000 mM KCl, 30 ml of the same buffer containing 1250 mM KCl, and 30 ml of the same buffer containing 1500 mM KCl. The active fractions were estimated from their UV absorbance at 220 nm.

Figure 3A:
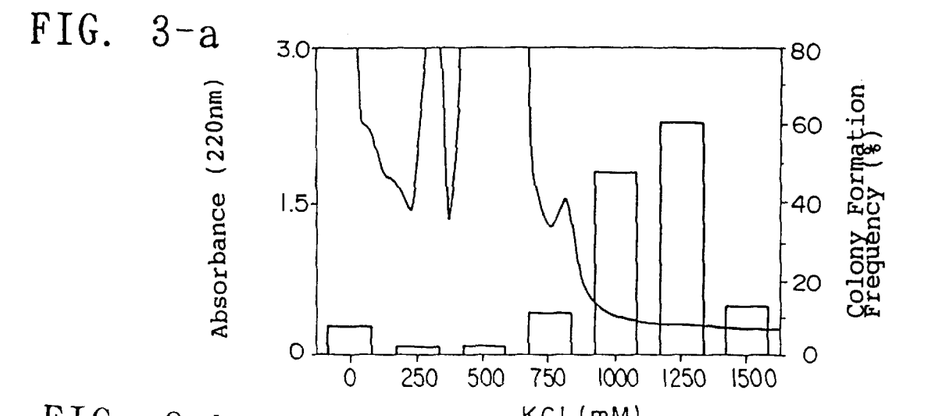

Fractions with plant cell growth-promoting activity were eluted with 1000 mM and 1250 mM KCl (FIG. 3-*a*). Only the fraction eluted with 1250 mM KCl was lyophilized. The weight was 9.02 mg.

Each eluate fraction was desalted through dialysis (Spectra/Por MWCO: 1000), and then concentrated to 50 ml.

Example 8

Gel Permeation Column

Figure 3B:
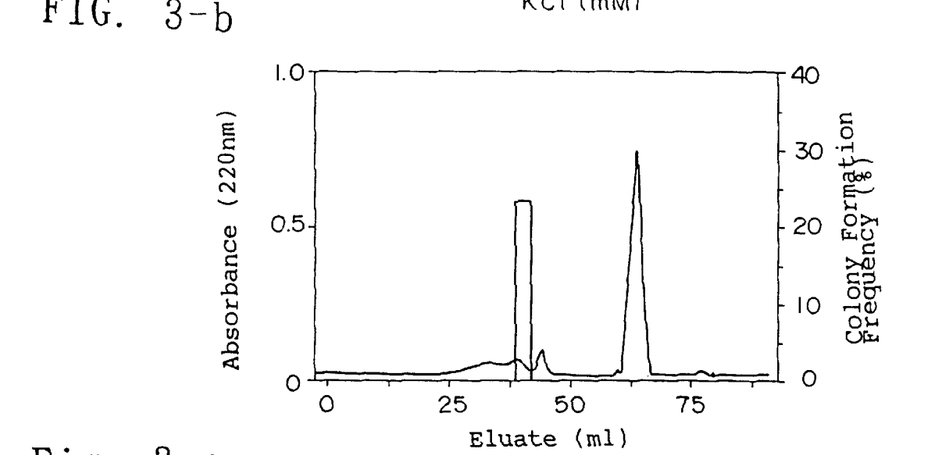

The desalted eluates obtained from the DEAE Sephadex column (fractions eluted with 1000 mM KCl and 1250 mM KCl) were lyophilized, and dissolved in 1.0 ml of 20 mM $KH_2PO_4$-KOH buffer (pH 5.8). Then, the resulting solution was put into a Bio-Gel P-2 extra fine column (1.7×37 cm) which was first equilibrated with the same buffer as that used for the previous dissolution. While monitoring the UV absorbance at 220 nm, the same buffer was applied to the column at a flow rate of 15 ml/hour (FIG. 3-*b*).

Fractions of 5 ml each were collected, and the activity of each fraction was determined through bioassay.

Example 9

Reversed-Phase HPLC Column

Figure 3C:
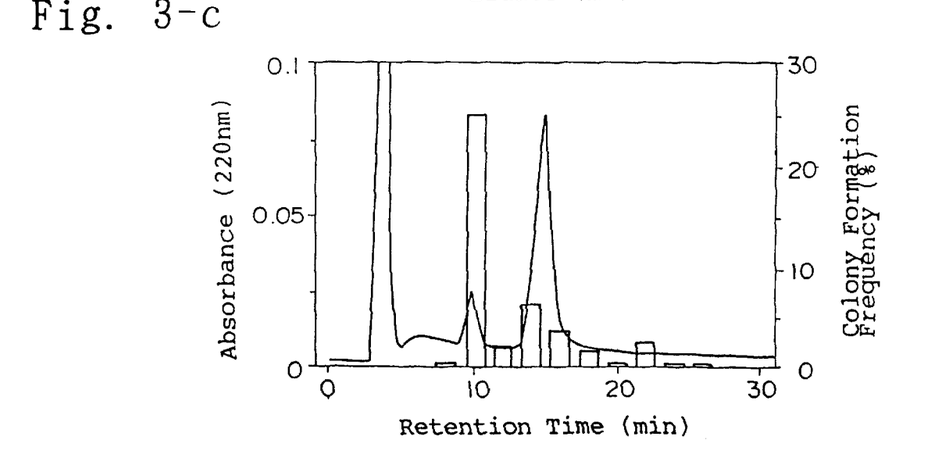

The active eluate fraction obtained from the Bio-Gel column was lyophilized, and then dissolved in 10 µl of 10% acetonitrile containing 0.1% TFA. The resulting solution was put into a Develosil ODS-HG-5 column (4.6×250 mm, produced by Nomura Chemical), and chromatographed according to isocratic elution with 10% acetonitrile containing 0.1% TFA at a flow rate of 1.0 ml/min, while monitoring the UV absorbance at 220 nm. Fractions of 2 ml each were collected, and their activity was determined through bioassay (FIG. 3-c). Two active fractions were collected. The yields from 600 ml of CM were 2 μg of compound (I-1) and 10 μg of compound (I-2). $10^7$-fold purification from CM was attained, and the recovery of the activity was 10%.

The fractions eluted in the above were examined for their amino acid composition as shown below.

Example 10

Amino Acids Sequence

As a result of the analysis of amino acids of compound (I-1) using a gaseous phase amino acid sequencer, compound (I-1) was found to be Tyr-Ile-Tyr-Thr-Gln. The molecular weight of compound (I-1) as determined through FAB-MS analysis was 846, which is larger by 160 than that of Tyr-Ile-Tyr-Thr-Gln.

In addition, pseudomolecular ions corresponding to $(M-2H+K)^-$ were observed at m/z 883; and fragment ions corresponding to $(M-H+80)^-$ were observed at m/z 765.

These results indicated that the amino acids constituting compound (I-1) were chemically modified, and that modification could be easily removed under the condition for the amino acid sequencing of the compound.

The observation of the fragment ions $(M-H+80)^-$ in the FAB-MS experiments indicated that compound (I-1) was a sulfated compound (Rogers et al.; Carbohydr. Res. Vol. 179, pp. 7–19, 1988), and the additional 160 mass units of compound (I-1), by which the molecular weight of compound (I-1) as measured through FAB-MS analysis was larger than the estimated molecular weight of the compound as calculated on the basis of the amino acid structure, were suggested to be sulfate groups with which the OH groups of the two tyrosine residues were substituted. Since the sulfate-substituted tyrosines are adsorbed to DEAE Sephadex, and the sulfuric acid moieties are removed under the condition for amino acid sequencing, the structure of compound (I-1) was determined.

To confirm the structure, compound (I-1) was synthesized. The unsulfated peptide was synthesized using a peptide synthesizer, and sulfate groups were incorporated on the peptide by arylsulfotranspeptidase (Muramatsu et al.; European Journal of Biochemistry, Vol. 223, pp. 243–248, 1944). The resulting peptide was eluted in reversed-phase HPLC at the same retention time as compound (I-1), and showed a mass spectrum that is characteristic of compound (I-1) in FAB-MS analysis. Furthermore, the resulting peptide exhibited the biological activity at the same concentrations as that of Compound (I-1).

Accordingly, the structure of compound (I-1) was also identified to be H-Tyr($SO_3H$)-Ile-Tyr($SO_3H$)-Thr-Gln-OH through its synthesis. In addition, amide derivative of compound (I-1), in which C-terminal carboxylic acid was amidated, was synthesized as compound (I-3).

As a result of the same test as above, the structure of compound (I-2) was identified to be H-Tyr($SO_3H$)-Ile-Tyr ($SO_3H$)-Thr-OH.

Moreover, according to the above-mentioned peptide synthesis, the following compounds were synthesized: compound (I-4) (SEQ ID NO: 4) having a structure of H-Tyr ($SO_3H$)-Val-Tyr($SO_3H$)-Thr-Gln-OH, which is different from compound (I-1) in that it has valine in place of isoleucine (FAB-MS m/z 831 $(M-H)^-$); compound (I-5) (SEQ ID NO: 5) having a structure of H-Tyr($SO_3H$)-Ile-Tyr ($SO_3H$)-Ser-Gln-OH, which is different from compound (I-1) in that it has serine in place of threonine (FAB-MS m/z 831 $(M-H)^-$); compound (I-6) (SEQ ID NO: 6) having a structure of H-Tyr($SO_3H$)-Ile-Tyr-Thr-Gln-OH, which is different from compound (I-1) in that one of two sulfotyrosine in the latter has been replaced with tyrosine (FAB-MS m/z 765 $(M-H)^-$); and compound (I-7) (SEQ ID NO: 7) having a structure of H-Tyr-Ile-Tyr($SO_3H$)-Thr-Gln-OH, which is different from compound (I-1) in that one of two sulfotyrosine in the latter has been replaced with tyrosine (FAB-MS m/z 765 $(M-H)^-$). Also synthesized was compound (I-8) (SEQ ID NO: 8) having a structure of H-Tyr-Ile-Tyr-Thr-Gln-OH, which is different from compound (I-1) in that the two sulfotyrosine in the latter have been replaced with tyrosines.

Reasonable variations, such as those that would occur to a skilled artisan, can be made herein without departing from the spirit and scope of the invention.

---

What is claimed is:

1. A peptide of the formula:

wherein one of $R^1$ and $R^2$ represents $SO_3H$ and the other represents $SO_3H$ or H; X represents an α-amino acid or a single bond; $Z^1$ and $Z^2$ are the same or different and each represents an α-amino acid; and Y represents OH or $NH_2$.

2. A plant growth promoter comprising the peptide as claimed in claim 1.

3. The peptide of claim 1, wherein the α-amino acid represented by X is glutamine.

4. The peptide of claim 1, wherein the α-amino acid represented by $Z^1$ is valine or isoleucine.

5. The peptide of claim 1, wherein the α-amino acid represented by $Z^2$ is serine or threonine.

6. A peptide of the formula:

wherein X represents glutamine or a single bond; and Y represents OH or $NH_2$.

7. The peptide of claim 6, wherein X is glutamine and Y is OH.

8. The peptide of claim 6, wherein X is a single bond and Y is OH.

9. A method of synthesizing the peptide of claim 1, comprising:

a) synthesizing a peptide skeleton of the formula:

wherein X represents an α-amino acid or a single bond; $Z^1$ and $Z^2$ are the same or different and each represents an α-amino acid; and Y represents OH or $NH_2$, and b) sulfating the peptide skeleton with an enzyme capable of bonding s sulfate group to the side chain of a tyrosine residue.

10. A method of promoting plant growth comprising administering the peptide of claim 1 to a plant.

11. The method of promoting plant growth of claim 10, wherein the plant is a monocotyledon.

12. The method of promoting plant growth of claim 11, wherein the monocotyledon is asparagus, rice or maize.

13. The peptide of claim 1, wherein the peptide functions as a plant growth factor.

14. A peptide of the formula:

wherein $R^1$ and $R^2$ are the same or different and each represents $SO_3H$ or H; X represents an α-amino acid or a single bond; $Z^1$ represents valine or isoleucine; $Z^2$ represents serine or threonine; Y represents OH or $NH_2$.

* * * * *